(12) United States Patent
Swain

(10) Patent No.: US 7,485,325 B2
(45) Date of Patent: *Feb. 3, 2009

(54) ANIMAL FOOD SUPPLEMENT COMPOSITIONS AND METHODS OF USE

(75) Inventor: Gayle Dorothy Swain, 418 Clabby, Weiser, ID (US) 83672

(73) Assignee: Gayle Dorothy Swain, Weiser, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/759,928

(22) Filed: Jun. 7, 2007

(65) Prior Publication Data

US 2007/0286913 A1    Dec. 13, 2007

Related U.S. Application Data

(63) Continuation-in-part of application No. 11/449,424, filed on Jun. 7, 2006, which is a continuation-in-part of application No. 10/636,331, filed on Aug. 6, 2003, now Pat. No. 7,067,161.

(60) Provisional application No. 60/812,026, filed on Jun. 7, 2006.

(51) Int. Cl.
*A61K 36/00* (2006.01)

(52) U.S. Cl. .................. 424/738; 424/439; 424/442

(58) Field of Classification Search .................. None
See application file for complete search history.

(56) References Cited

U.S. PATENT DOCUMENTS

| 4,588,589 A * | 5/1986 | Sheth et al. .................. 424/738 |
| 5,009,916 A | 4/1991 | Colliopoulos |
| 5,120,362 A | 6/1992 | Kauffman |
| 5,232,699 A | 8/1993 | Colliopoulos |
| 5,464,644 A | 11/1995 | Wullschleger et al. |
| 5,516,798 A * | 5/1996 | Ferket .................. 514/556 |
| 5,656,312 A | 8/1997 | Erasmus et al. |
| 6,042,857 A | 3/2000 | Jones et al. |
| 6,451,370 B1 | 9/2002 | Anderson |
| 7,067,161 B2 * | 6/2006 | Swain .................. 424/738 |

FOREIGN PATENT DOCUMENTS

| WO | WO 98/39980 | 9/1998 |
| WO | WO 98/43493 | 10/1998 |
| WO | WO 02/26213 A1 | 4/2002 |

OTHER PUBLICATIONS

Twin Valley Agri-Products, "Psylhusk Pellets," Dec. 2002, 2 pages.
Twin Valley Agri-Products, "Psylhusk Pellets," Apr. 2003, 2 pages.
"Animal Health, Educating Your Market," Made in Australia, date unknown (estimate Sep. 10, 2002), pp. 14-15.
Mair, Tim et al., Medical Treatment of Equine Colic, In Practice, Nov./Dec. 1998, vol. 20, No. 10, pp. 578-584.
Castleman, Michael, The Healing Herbs, The Ultimate Guide to the Curative Power of Nature's Medicines, pp. 37-39, 1991, Rodale Press, Emmaus, PA.
Psylhusk Pellets website (http://web.archive.org/web/20030302030604/www.psylhusk.com/psylhusk+pellets_.htm)—Nov. 2003, printed Aug. 8, 2007.
http://www.horses-and-horse-information.com/articles/1295colic.shtml, published Winter 1995, printed Aug. 9, 2007.

* cited by examiner

*Primary Examiner*—Susan C Hoffman

(57) ABSTRACT

An animal food supplement particularly useful in treating gastrointestinal problems, such as colic. Psyllium husks are provided in dry form for convenience of handling prior to feeding. In examples of embodiments, psyllium husks are admixed with binding material and the admixture is formed into pellets, crumbles, mashes, or licks. Upon consumption by the animal, the psyllium husks take up water from the moist environment of the animal's gastrointestinal tract and form a gelatinous bolus that sweeps through the gastrointestinal tract of the animal, clearing the gastrointestinal tract of intestinal detritus, such as sand, toxins, and microorganisms, which agglomerate with and/or are carried away by the psyllium husk gel.

13 Claims, 3 Drawing Sheets

ANIMAL FOOD SUPPLEMENT COMPOSITIONS AND METHODS OF USE

CROSS-REFERENCE TO RELATED APPLICATIONS

This application claims the benefit under 35 U.S.C. § 119 (e) of U.S. Provisional Application No. 60/812,026, filed Jun. 7, 2006, and is also a continuation-in-part of application Ser. No. 11/449,424, filed Jun. 7, 2006, pending, which is a continuation-in-part of application Ser. No. 10/636,331, filed Aug. 6, 2003, now U.S. Pat. No. 7,067,161, issued Jun. 27, 2006. The disclosure of each of the previously referenced U.S. patent applications and patents referenced is hereby incorporated by reference in its entirety.

BACKGROUND OF THE INVENTION

1. Field of the Invention

The present invention relates to animal food supplement compositions and methods of using the same, the compositions being particularly useful in relation to, but not limited to, treatment of colic and other gastrointestinal problems in animals.

2. State of the Art

Animal healthcare is an important consideration in many aspects of the economy, such as in food production, research, education (e.g., in zoos) and animal competitions (e.g., horse racing). Productivity, cost control and profitability in these areas of the economy are improved when the health of the animals involved is improved. Efficient and cost-effective animal healthcare is especially important where a substantial investment is required to raise animals to maturity, as is the case with horses.

Animals frequently ingest sand, soil, and other extraneous materials when they are grazing or feeding from a feed box that contains such contaminants. Over time, deposits of these extraneous materials accumulate in the digestive system of the animal, causing colic. Colic generally refers to malfunction, swelling, infection, or blockage in the gastrointestinal tract of an animal. As used herein, the term "intestinal detritus" refers to the aforementioned ingested sand, soil, and other extraneous materials accumulated in the gastrointestinal tract of an animal.

Instances of colic are particularly distressing for the animal and for the owner, because colic is frequently painful to the animal and difficult to identify and treat. Though an owner may try numerous treatments to relieve the animal's symptoms, unfortunately, previously known treatments often prove ineffective and, unfortunately, animals regularly die as a result of colic. For example, approximately one in ten horses with colic die because no effective treatment has been available in the past.

In economically significant animals such as horses, cattle, swine, chickens, broilers, quail, pheasants, turkeys, ostrich, emus, and other exotic birds, gastrointestinal problems such as colic pose a major economic threat. As a result, means for reducing the economic impact of colic, i.e., cost-effective treatments for colic, are in great demand.

The present invention overcomes, at least in part, some of the aforementioned disadvantages of prior art treatments for colic and other gastrointestinal problems in animals.

BRIEF SUMMARY OF THE INVENTION

The present invention provides an animal food supplement particularly useful in treating gastrointestinal problems, such as colic, in horses, cattle, swine, chickens, broilers, quail, pheasants, turkeys, ostrich, emus, and other exotic birds. Psyllium husk is the only natural gelatinous and hygroscopic material that is suitable for consumption by both humans and animals, so it is abundantly available. According to the present invention, psyllium husk may be provided in dry form for convenience of handling prior to feeding. In currently preferred embodiments, psyllium husks may be admixed with binding material having low moisture content, and the admixture is formed into pellets, crumbles, mash, or licks. Upon consumption by the animal, the psyllium husk material takes up water from the moist environment of the animal's gastrointestinal tract and forms a gelatinous bolus that sweeps through the animal's gastrointestinal tract, clearing intestinal detritus, such as sand, soil, toxins, and microorganisms, which agglomerates with and/or is carried away by the psyllium husk gel.

A first aspect of the present invention includes an animal food supplement composition including psyllium husk. The animal food supplement may further comprise creatine.

A second aspect of the present invention includes a pharmaceutical composition comprising an animal food supplement composition as an active ingredient optionally admixed with a pharmaceutically acceptable carrier, the animal food supplement composition including psyllium husk.

A third aspect of the present invention includes a method of using an animal food supplement composition for the preparation of medicaments for the treatment of animal gastrointestinal problems, such as horse colic, wherein the animal food supplement composition includes psyllium husk.

A fourth aspect of the present invention includes a packaged animal food supplement composition comprising a substantially hermetic packaging material containing the animal food supplement composition and an atmosphere with a reduced oxygen content in comparison to ambient air.

A fifth aspect of the present invention includes a method of using an animal food supplement composition including psyllium husk for reducing the need for antibiotics to be given to an animal.

A sixth aspect of the present invention includes a method of using an animal food supplement composition including psyllium husk to increase the content of *Bacteroides thetaiotaomicron* in the gastrointestinal tract of an animal.

A seventh aspect of the invention includes a method of using an animal food supplement composition including psyllium husk to decrease the gastrointestinal content of organisms other than *Bacteroides thetaiotaomicron* in an animal.

An eighth aspect of the invention includes a method of increasing the rate of growth during a growth period in an animal by providing an animal food supplement composition including psyllium husk to the animal before or during the growth period.

A ninth aspect of the invention includes methods of optimizing a feeding regime including an animal food supplement composition comprising psyllium husk, the method comprising monitoring the bacterial content in the feces of an animal.

A tenth aspect of the invention includes a method of eradicating rodents comprising distributing in a area where rodents are present, a food supplement composition comprising psyllium husk material and at least one binding agent for binding the psyllium husk material in a desired physical form.

An eleventh aspect of the invention includes feeding or treating the animal species listed in the appendix of additional information of U.S. Provisional Patent Application Ser. No. 60/812,026, filed Jun. 7, 2006, hereby incorporated herein by this reference (hereinafter referred to as "the appendix") with a food supplement composition comprising psyllium husk material. Another aspect includes treating animals for the diseases and health states provided in the appendix of additional information with a food supplement composition comprising psyllium husk material.

The present invention advantageously may be incorporated in the ordinary diet of an animal as a treatment for, or preventive measure against, colic and other gastrointestinal problems. An additional advantage of the present invention is that it requires only the use of natural ingredients.

Further advantages of the present invention over the state of the art include (but are not limited to) the provision of the animal food supplement according to the invention in a pellet, crumble, mash, or lick form that has a low nutritional value so as to avoid interference with or disruption of the diet of the treated animal and to provide a convenient means by which medication or other dietary supplements, such as vitamins and minerals, may be added to the animal's diet. Through the practice of the present invention, an animal's gastrointestinal tract is cleansed of indigestible matter and toxic deposits for, as appropriate, the prevention and treatment of gastrointestinal problems and improvement of the overall health and well-being of the animal, one result of which is improved economic productivity associated with the animal.

In the drawings, which illustrate what is currently considered to be the best mode for carrying out the invention:

DETAILED DESCRIPTION OF THE INVENTION

The present invention makes beneficial use of the hygroscopic properties of psyllium husks. Psyllium husks swell when they come into contact with water and, thus, are difficult to handle conveniently when mixed with conventional animal feeds that have a high moisture content, such as molasses and water. Accordingly, it is preferred to provide psyllium husks in dry form for convenience in handling. Upon consumption by the animal, the psyllium husks take up water from the moist environment of the animal's gastrointestinal tract and form a gelatinous bolus that sweeps through the gastrointestinal tract of the animal, clearing the gastrointestinal tract of intestinal detritus, such as sand, soil, toxins, and microorganisms, which agglomerate with and/or are carried away by the psyllium husk gel.

However, certain animals, such as horses, will not voluntarily eat dry, unbound psyllium husk material because it is unpalatable. Thus, the mere addition of dry unbound psyllium husks to a feed box is ineffective since the animal may never actually consume the psyllium husks despite their inclusion in the feed box. Accordingly, the present invention provides an animal food supplement that is designed to be palatable to animals for which it is intended, e.g., by using flavors, aromas and textures that appeal to the animal to be treated. The selection of flavors, aromas, and textures appropriate for a given subject, i.e., the design of a palatable product, is well within the skill of the ordinary artisan and is, therefore, not discussed further here.

Figure 1:
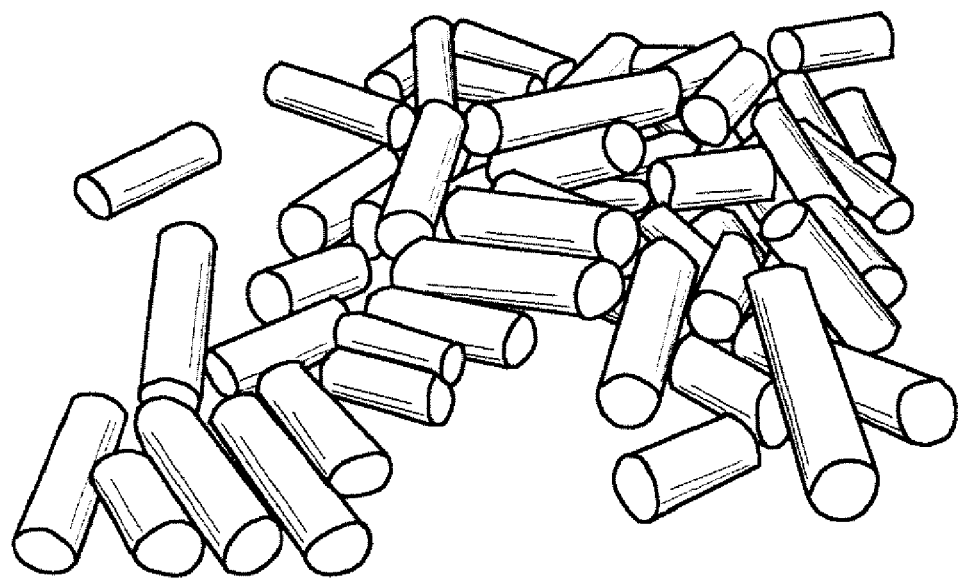
FIG. 1 is a graphical depiction of a pellet physical form of the food supplement composition of the invention.
Figure 2:
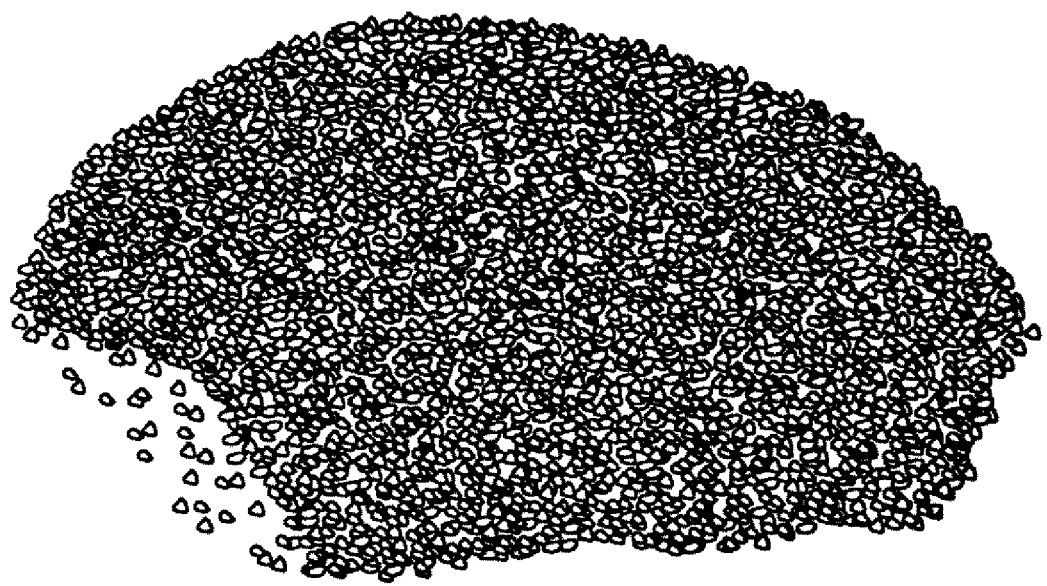
FIG. 2 is a graphical depiction of a crumble physical form of the food supplement composition of the invention.
Figure 3:
FIG. 3 is a graphical depiction of a mash physical form of the food supplement composition of the invention.
Figure 4:
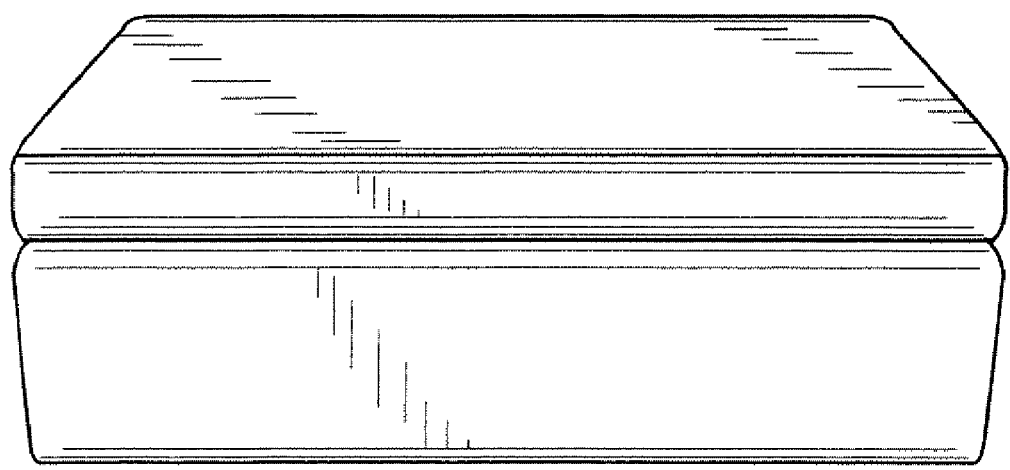
FIG. 4 is a graphical depiction of a lick physical form of the food supplement composition of the invention.

To overcome problems associated with the hygroscopicity of psyllium husks, the present invention provides an animal food supplement prepared from psyllium husks mixed together with a relatively low moisture content binding agent. Preferably, the animal food supplement is extruded into pellet form (as depicted in FIG. 1) for ease of inclusion into the animal's feed box and to ensure consumption thereof by the animal. However, it is also envisaged that the animal food supplement of the invention may be manufactured in a crumble form (as depicted in FIG. 2), a mash form (as depicted in FIG. 3), or an animal lick form (as depicted in FIG. 4).

The animal food supplement of the present invention contains from 0 to about 95 percent by weight of psyllium husks in seed, powdered or granulated form, including particulate material comprising stalk, flower and leaf fragments with up to 0 to about 75 percent impurities. It is currently preferred that the food supplement contain about 50 percent psyllium husks. Most preferably according to present beliefs, the food supplement should contain about 30 percent to 35 percent psyllium husks.

The animal food supplement of the present invention may also contain from 0 to about 95 percent grain by-products, including oats, barley, maize, lupins, lupin hulls, mill mix, mill run, pollard, bran, canola meal, soya meal in a rolled, crushed or powdered form, or a mixture thereof; from 0 to about 95 percent lucerne in either chaff, hay, fines or powder form, or a mixture thereof; from 0 to about 95 percent oaten, wheaten or meadow hay in chaff, fines or powder form, or a mixture thereof; and/or from 0 to about 95 percent molasses, and, optionally, additional vitamins and minerals.

The animal food supplement of the present invention may also contain creatine. Creatine is known in the art, among other benefits, to help increase muscle mass. Creatine may be present from 0 to 95 percent by weight. Further, the animal food supplement of the present invention may be formulated to contain from about 1 mg to about 40,000 mg of creatine per serving.

To avoid interference with or disruption of the animal's diet, the food supplement of the invention preferably contains less than about 8 percent protein.

It is currently preferred that the moisture content of an animal food supplement according to the invention be approximately 11 percent to 14 percent. It is also currently preferred that an animal food supplement according to the invention contain between about 7.5 percent and 10 percent lucerne in either chaff, hay, fines or powder form, or a mixture thereof.

Pellets of the animal food supplement of the invention are prepared by rolling, crushing and/or powdering grain by-products and other binding agents as described above to achieve a substantially homogenously sized mixture. Psyllium husks are then added to the mixture, whereupon the mixture is treated with steam and extruded through dies, which may range, for example, from 2 mm to 10 mm in aperture size to form pellets.

The use of proper packaging of the food supplement of the invention is also a significant consideration. If exposed to ambient air, the flavor, aroma and texture of the supplement degrade undesirably over time. However, vacuum packaging is not suitable because the supplement is best preserved if it is allowed to "breathe" without being exposed to ambient air. Thus, another advantageous aspect of the invention is specialized packaging that prevents or reduces the aforementioned degradation.

Figure 5:
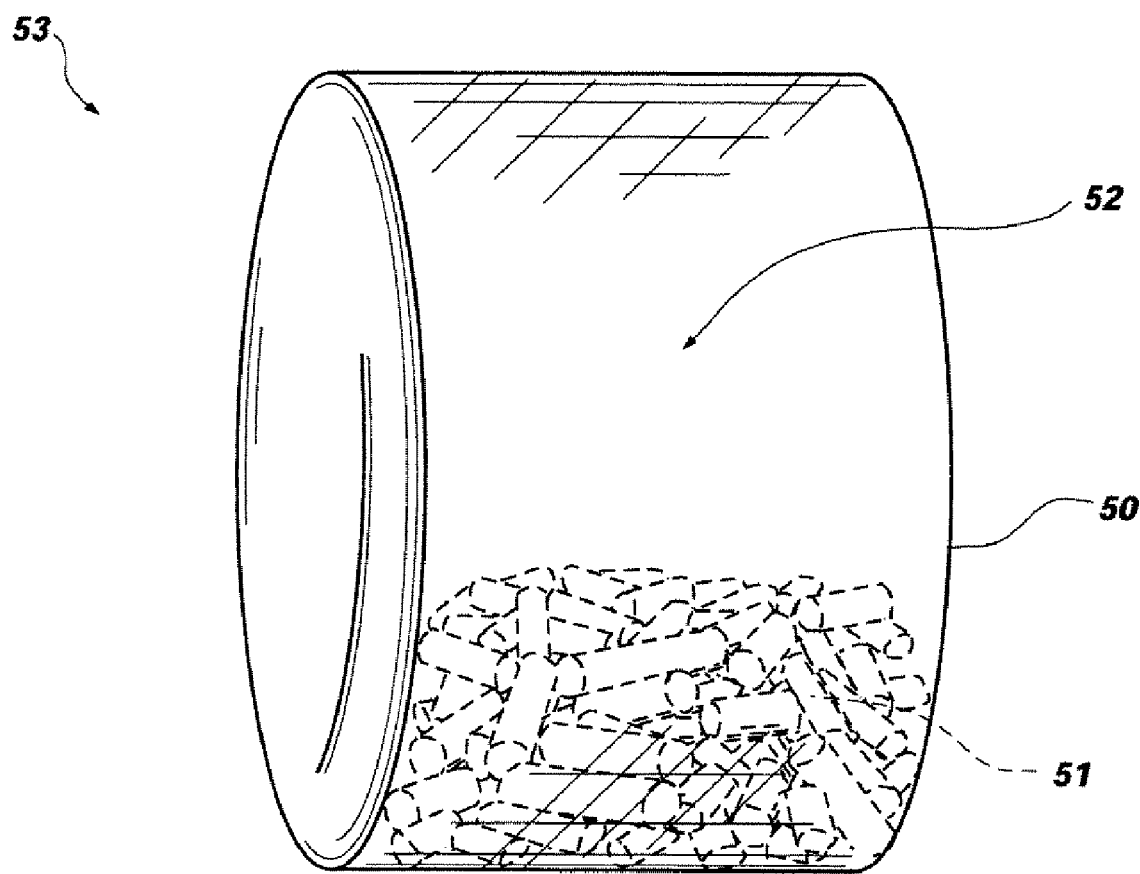
FIG. 5 is a graphical depiction of a specialized package containing the food supplement composition of the invention.

Referring to FIG. 5, the packaging according to the invention is substantially hermetic, and a reduced oxygen content atmosphere such as an inert gas, for example, nitrogen, may be introduced into the package during filling thereof with the supplement in an appropriate form (for example, pellets) to displace ambient air present inside the package, providing a sealed environment, generally indicated at 50, containing the supplement 51 and an atmosphere 52 including less oxygen than ambient air 53. Thus, packaging is provided that allows the food supplement of the invention to "breathe" the atmosphere within the package while preventing or at least reducing the degradation caused by exposure to ambient air. Currently preferred are 3-ply paper sacks, in which one ply is a 40 μm BOPP liner, supplied by Australian Multiwall Bag Co. Pty. Ltd. (Murdoch, Australia).

In use, the animal food supplement composition may be introduced in pellet form, for example, into the feed box of an animal that is exhibiting symptoms of gastrointestinal problems, such as colic. In an example of a treatment for an adult horse, a dose of about 500 g of the composition is provided on the first day of treatment, a dose of about 850 g of the composition is provided on the second day of treatment, a dose of about 1000 g of the composition is provided on the third day of treatment, a dose of about 2000 g of the composition is provided on the fourth day of treatment, and a final dose of 2500 g of the composition is provided on the fifth day of treatment.

During administration of the food supplement of the present invention, the animal must drink plenty of fresh water on a regular basis, otherwise serious injury may result.

The food supplement of the present invention was tested against a placebo in horses. The feces of the horses were monitored for clearance of intestinal detritus, and x-ray imaging was also used to monitor movement of material through the gastrointestinal tracts of the horses. One group of horses was administered the food supplement of the invention according to the above schedule, while a control group was fed a placebo according to the same schedule. All horses that received the food supplement of the invention cleared accumulated intestinal detritus (sand) during the course of treatment, while those in the placebo group either did not clear or cleared very little intestinal detritus. Horses receiving the food supplement of the invention passed as much as ¼ gallon of sand in feces in a 24-hour period during treatment.

In addition, it was also observed that the general health and performance of the animals were improved after receiving the food supplement of the present invention. After treatment, animals were observed to excrete less undigested feed, the condition of their coats improved, and even some inexplicable behavioral problems were resolved. Further, animals receiving the food supplement of the present invention during growth phases demonstrate greater than normal growth increases in mass. While not intending to be bound to any particular theory of action, the inventor believes that promotion of symbiotic bacteria in conjunction with clearance of intestinal detritus and non-symbiotic bacteria through administration of the food supplement of the present invention is useful in promoting growth of the animals, reducing the amount of antibiotics that need to be given to an animal, and in treating not only colic, but also other problems that may be related to gastrointestinal blockage and/or accumulation, such as equine ulcers and founder.

There is only one symbiote presently known to colonize the human gut—*Bacteroides thetaiotaomicron*. This anaerobic organism is thought to aid digestion thought breakdown of complex carbohydrates into simpler molecules that can be taken up by the gut. Further, it has been recently found that the goblet cells of the intestine, which are normally thought to secrete mucus, secrete packets of cytoplasm containing large numbers of mitochondria. It is currently thought that these mitochondria aid in the creation of a permissive anaerobic environment for *Bacteroides thetaiotaomicron* through the consumption of available oxygen in the gut. The mucus secreted by the goblet cells (a glycoprotein similar to that found in the food supplement of the present invention) may also be used to provide a food source to the symbiotic bacteria population in the absence of normal food. For this reason, the glycoprotein present in the food supplement of the present invention should not effect the growth, and may even promote the growth, of the symbiotic bacteria. In contrast, most other normal gut flora (e.g., *E. coli*) do not grow well (or at all) when streaked across agar plates containing a dilute solution of the food supplement of the present invention.

In relation to the increased growth noted in immature animals fed with the food supplement of the present invention, the increased growth may be due to the promotion of the symbiotic bacteria by 1) providing at least a neutral composition or possible a food source for the symbiotic bacterium, or 2) removing or preventing the growth of other flora allowing the symbiotic bacteria to better compete for limited space and food sources. As the symbiotic bacteria population rises, more of the symbiotic bacteria are available for the breakdown of foodstuffs containing complex carbohydrates providing to the animal more useful energy per unit of food consumed, leading to better growth.

Research is ongoing to determine whether equine ulcers are caused by bacteria, as are ulcers in humans. If so, the food supplement of the present invention may be useful in preventing, as well as treating, equine ulcers by clearing the equine gut of bacterial deposits. Further, it is believed that founder (chronic laminitis) can be caused by toxic accumulations in the caecum, which kill off beneficial bacteria and damage the wall of the caecum. The damaged tissue of the caecum diverts resources such as glucose from the bloodstream as it heals, and founder is believed to result from insufficient nutrient supply to the hoof. Thus, the present invention is likely useful in treating a variety of animal health problems, as well as for promoting and maintaining general gastrointestinal health in animals.

The food supplement of the present invention is useful in many kinds of animals such as, for example, horses, cattle, swine, cats, dogs, chickens, broilers, quail, pheasants, turkeys, ostrich, emus, and other exotic birds. Of course, it is contemplated that the number of days of treatment and the dosages applied to each of these species will vary depending upon the size of the animal and the severity of the symptoms that it exhibits. For example, weanling and yearling horses may be fed at half the rate of an adult horse, and miniature ponies may be administered a dose of one third cup per day for five days. One of ordinary skill in the art in the health care of a given animal will readily be able to determine an appropriate dosage regimen. In general, it is currently preferred to administer the food supplement of the invention for five days with gradually increasing daily doses.

The above-mentioned treatment schedule, or one similar thereto, may be repeated every ten weeks as a preventive treatment against colic or other gastrointestinal problems.

In one example of an embodiment of the present invention, a method of increasing the content of *Bacteroides thetaiotaomicron* in the gut of an animal is disclosed. The method comprises feeding to the animal a food supplement according to the present invention. The content *Bacteroides thetaiotaomicron* in the gut of the animal may be monitored using standard techniques. An example of such a technique includes, but is not limited to, assaying the number of *Bacteroides thetaiotaomicron* in a feces sample by spreading the sample on agar plate containing components known to promote the growth of *Bacteroides thetaiotaomicron* and placing the agar plate in an anaerobic environment. After a number of days, the *Bacteroides thetaiotaomicron* content may be determined by counting the number of *Bacteroides thetaiotaomicron* plaques that grow on the plates.

A further example of such a technique includes, but is not limited to, performing PCR (Polymerase Chain Reaction) on a feces sample using species specific promoters directed to *Bacteroides thetaiotaomicron*, and relating the number of copies produced to the *Bacteroides thetaiotaomicron* content in the feces sample.

In a further example of an embodiment of the present invention, a method of decreasing, in an animal, the gastrointestinal content of organisms other than *Bacteroides thetaiotaomicron* is disclosed. The method comprises feeding to the animal a food supplement according to the present invention. The content of organisms other than *Bacteroides thetaiotaomicron* in the gut of the animal may be monitored using standard techniques. An example of such a technique includes, but is not limited to, assaying the number of organisms other than *Bacteroides thetaiotaomicron* in a feces sample by spreading the sample on an agar plate containing components known to promote the growth of bacteria generally and placing the agar plate in an environment known to promote the growth of bacteria. After a number of days, the bacterial content may be determined by counting the number of bacterial plaques that grow on the plates.

A further example of such a technique includes, but is not limited to, performing PCR on a feces sample using species specific promoters directed to bacteria other than *Bacteroides thetaiotaomicron*, and relating the number of copies produced to the bacteria content in the feces sample.

In another example of an embodiment of the present invention, a method of decreasing the need for antibiotics to be given to an animal is disclosed. The method comprises feeding to the animal a food supplement according to the present invention. The need for antibiotics can be correlated to the bacterial content of organisms other than *Bacteroides thetaiotaomicron* in the gut of the animal. The content of organisms other than *Bacteroides thetaiotaomicron* in the gut of the animal may be monitored using standard techniques. An example of such a technique includes, but is not limited to, assaying the number of organisms other than *Bacteroides thetaiotaomicron* in a feces sample by spreading the sample on an agar plate containing components known to promote the growth of bacteria generally and placing the agar plate in an environment known to promote the growth of bacteria. After a number of days, the bacterial content may be determined by counting the number of bacterial plaques that grow on the plates.

A further example of such a technique includes, but is not limited to, performing PCR on a feces sample using species specific promoters directed to bacteria other than *Bacteroides thetaiotaomicron*, and relating the number of copies produced to the bacteria content in the feces sample.

In a yet further example of an embodiment of the present invention, a method of increasing the rate of growth of an immature animal is disclosed. The method comprises feeding to the animal a food supplement according to the present invention prior or during a growth phase in the animal. Growth rate may be increased by 1 percent to 200 percent for a given growth phase when compared to normal, or the increase may be in the overall growth of the animal over time when compared to normal.

In an additional example of an embodiment of the present invention, a method of optimizing a feeding regime is disclosed. The method comprises monitoring the bacterial content in the gut or the growth rate of an animal being fed the food supplement according to the present invention and adjusting the amount of food supplement according to the present invention being fed to an animal based on the bacterial content in the gut or the growth rate of the animal. Growth rate can be measured using standard techniques. Such techniques include, but are not limited to, body mass, body mass index, height, or displacement. Bacterial content in the gut can be monitored as detailed supra. The amount of food supplement in the diet of the animal can be adjusted in reference to growth rate or bacterial content in the gut to achieve the highest growth rate or an optimal bacterial content.

Surprisingly, the food supplement of the present invention was also discovered to eradicate rodent pests. Rodents that consume the food supplement of the invention die, presumably because the hygroscopic swelling of the psyllium husks blocks or bursts the rodent's gastrointestinal tract. This unexpected benefit of the present invention is particularly advantageous because the same material can be used concurrently to treat gastrointestinal problems in economically significant animals and to eradicate rodent pests.

Other examples of embodiments according to the invention include feeding or treating the animal species listed in the appendix of additional information with a food supplement composition comprising psyllium husk material. Other examples of embodiments according to the invention include treating animals for the diseases and health states provided in the appendix of additional information with a food supplement composition comprising psyllium husk material.

EXAMPLES

The present invention is further described in the following examples, which are offered by way of illustration and are not intended to limit the invention in any manner.

Example 1

Animal Food Product Suitable for Feline Use

An animal food product suitable for feline use may contain from about 1.5 to about 2 oz./pound of psyllium husk and may also contain about 0 to about 95 percent of any of mill mix, ground barley, alfalfa fines, flavoring and/or seasonings at less than 0.5 percent by weight, vitamin and mineral pre-mix, corn germ meal, liver, air dried organic alfalfa, dried barley juice, yucca baccatta, American Indian wild rhubarb (rumex hymenosepalus toor), live yeast powder, ester C, uncaria tomentosa, whey powder, dicalcium phosphate, seaweed meal dehydrated, amino acid chelates of iron, manganese, zinc magnesium, potassium, copper and cobaltite (yeast bound), Vitamin A supplement, deactivated animal terol (source of Vitamin D), Vitamin E supplement, Vitamin B12 supplement, honey bee pollen, sodium selenite (yeast bound).

A feeding regime of such an animal food product suitable for feline use may comprise adding two teaspoonfuls of the animal food product suitable for feline use to the feed bowl twice a day.

An animal food product suitable for feline use may comprise 5 ounces 95 percent to 98 percent purity of psyllium husk and 0.05 percent mineral mixture.

An animal food product suitable for feline use may be used as a treatment for the treatment of mega colon in felines or other animals. A method of treating mega colon in a feline or other animal may include feeding to the feline or other animal ¼ teaspoon of the animal food product suitable for feline use in combination with wet food four times per day.

Benefits of such an animal food product suitable for feline use may include, but are not limited to, removing the smell from the litter tray by removing the bacteria from the stool and encapsulating the content in the gel, better absorption of food, allow a clean gut, greater nutritional benefit from foods of nutritive value, aid pregnant animals produce strong healthy offspring, aid lactating animals to produce high quality milk, and offspring grow quickly and develop strong bodies early in their life. The development of the glycoproteins as a result of feeding psyllium husk may encourage the reduction of pathogens in the body resulting in less illness.

As will be appreciated by one of skill in the art, although the foregoing example has been directed to an animal food product suitable for feline use, such an animal food product may be suitable for any other animal.

Example 2

Animal Food Product Suitable for Poultry Use

An animal food product suitable for poultry use may contain from about 1.5 to about 2 oz./pound of psyllium husk and may also contain about 0 to about 95 percent of any of, cracked corn, whole wheat, soyabean meal, oyster shell monocalcium phosphate, dicalcium phosphate, calcium carbonate, ALT, di-methionine, Vitamin A acetate, Vitamin B12 supplement, biotin calcium pantothenate, coline chloride folic acid, niacin, pyridoxine hydrochloride, riboflavin supplement, calcium iodate, copper sulfate, ferrous sulfate, mangenous oxide, sodium selenite, zinc oxide, iron oxide, and mineral oil.

An animal food product suitable for poultry use may be manufactured by blending the ingredients into a crumble mix—starter/grower—layer. An animal food product suitable for poultry use may be packaged in 50-pound bags and the bags may be poly/woven bags.

Benefits of such an animal food product suitable for avian use may include, but are not limited to, growing birds to size in approximately ⅔ normal growing time, therefore mature for market earlier, may be used as a partial or full substitute for hormones/steroids and antibiotics in a poultry diet.

An animal food product suitable for poultry use may be manufactured by blending the ingredients into a crumble mix—starter/grower—layer or formed into pellets or 3 mm to 4 mm in size.

The development of the glycoproteins as a result of feeding psyllium husk may encourage the reduction of pathogens in the body resulting in less illness. Illness that might be treated using an animal food product suitable for poultry use include, but are not limited to, *salmonella* and paracolon infections, pullorum disease, fowl typhoid, coliform infections, *staphylococcus* and *streptococcus* infections, fowl cholera, erysipelas, and avian vibrionic hepatitis.

As will be appreciated by one of skill in the art, although the foregoing examples have been directed to an animal food product suitable for poultry use, such an animal food product may be suitable for any other animal, such as, but not limited to, chicken, turkey, duck, quail, wild birds, and chickens.

Example 3

Animal Food Product Suitable for Swine Use

An animal food product suitable for swine use may contain from about 16 percent to about 20 percent protein. An animal food product suitable for swine may contain 1⅔ cup of psyllium husk per daily ration or may contain 1.6 oz of psyllium husk distributed over a daily ration of for example, three pounds of animal food product per day. An animal food product suitable for swine may contain from about 0 to about 95 percent of any of, cracked corn, soya bean meal, fat, mono calcium phosphate, dicalcium phosphate, calcium carbonate, salt, L-Lysine monochloride, Vitamin A acetate, Vitamin B3 supplement, Vitamin E supplement, Vitamin K, Vitamin B12 supplement, biotin, calcium pantothenate, choline chloride, folic acid, niacin, pyridoxine hydrochloride, riboflavin supplement, calcium iodate, copper sulfate, ferrous sulfate, mangenous oxide, sodium selenite, zinc oxide, iron oxide, and mineral oil.

The development of the glycoproteins as a result of feeding psyllium husk may encourage the reduction of pathogens in the body resulting in less illness. Illness that might be treated using an animal food product suitable for swine use include, but are not limited to, ileitis, spirochetal colitis, swine dysentery, transmissible gastroenteritis, epidermic diarrhea virus, Salmonellosis, *Escherichia coli*, clostridium difficle, clostridial enteritis, coccidiosis, colitis nonspecific, gastric ulceration, parasites, and TGE virus.

Although the present invention has been described with respect to the currently preferred embodiments set forth herein, various additions, deletions and modifications are contemplated as being within its scope. The scope of the invention is, therefore, indicated by the ensuing claims, rather than the foregoing description. All changes that come within the meaning and range of equivalency of the claims are to be embraced within their scope.

What is claimed is:

1. A solid food supplement composition for a non-human animal, comprising:
    between about 30 percent to 35 percent psyllium husk material;
    less than about 8 percent protein;
    between about 7.5 percent to 10 percent lucerne;
    at least one binding agent binding the psyllium husk material in a desired physical form;
    creatine; and
    a moisture content of approximately 11 percent to 14 percent.

2. The food supplement composition of claim 1, wherein the creatine is present at from about 0.001 percent to 95 percent by weight.

3. The food supplement composition of claim 1, wherein the food supplement composition is sufficiently low in nutritional value so as to avoid interference with or disruption of the diet of the non-human animal ingesting the food supplement composition.

4. The food supplement composition of claim 1, further comprising at least one grain by-product selected from the group consisting essentially of oats, barley, maize, lupins, lupin hulls, bran, canola meal, and soya meal.

5. The food supplement composition of claim 1, further comprising hay.

6. The food supplement composition of claim 5, wherein the hay is at least one of oaten, wheaten, and meadow hay.

7. The food supplement composition of claim 1, further comprising at least one pharmaceutical composition.

8. The food supplement composition of claim 1, further comprising at least one nutrient.

9. The food supplement composition of claim 8, wherein the at least one nutrient is at least one of a vitamin and a mineral.

10. The food supplement composition of claim 1, wherein the desired physical form is a pellet, a crumble, a mash, or a lick.

11. The food supplement composition of claim 1, further comprising a flavoring.

12. The food supplement composition of claim 1, wherein the flavoring includes molasses.

13. A substantially hermetic package containing a solid food supplement composition, the substantially hermetic package containing an atmosphere having less oxygen than ambient air, the solid food supplement composition comprising:

between about 30 percent to 35 percent psylliuin husk material;

less than about 8 percent protein;

between about 7.5 percent to 10 percent lucerne;

at least one binding agent for binding the psyllium husk material in a desired physical form;

creatine; and a moisture content of approximately 11 percent to 14 percent.

* * * * *